(12) United States Patent
Adams

(10) Patent No.: US 8,062,261 B2
(45) Date of Patent: Nov. 22, 2011

(54) CONTROLLED FLASHBACK FOR VASCULAR ACCESS DEVICES

(75) Inventor: Chad M. Adams, Cedar Hills, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 766 days.

(21) Appl. No.: 11/680,298

(22) Filed: Feb. 28, 2007

(65) Prior Publication Data

US 2007/0233007 A1 Oct. 4, 2007

Related U.S. Application Data

(60) Provisional application No. 60/777,841, filed on Mar. 1, 2006.

(51) Int. Cl.
A61M 5/178 (2006.01)
(52) U.S. Cl. .............................. 604/167.03; 604/168.01
(58) Field of Classification Search .............. 604/167.01
See application file for complete search history.

(56) References Cited

U.S. PATENT DOCUMENTS

| | | | |
|---|---|---|---|
| 4,269,186 A * | 5/1981 | Loveless et al. ......... | 604/168.01 |
| 4,365,630 A | 12/1982 | McFarlane | |
| 4,387,879 A | 6/1983 | Tauschinski | |
| 4,512,766 A | 4/1985 | Vaillancourt | |
| 4,525,157 A | 6/1985 | Vaillancourt | |
| 4,790,817 A * | 12/1988 | Luther ......................... | 604/509 |
| 4,842,591 A | 6/1989 | Luther | |
| 4,874,377 A | 10/1989 | Newgard et al. | |
| 4,917,668 A | 4/1990 | Haindl | |
| 4,966,586 A | 10/1990 | Vaillancourt | |
| 5,032,116 A | 7/1991 | Peterson et al. | |
| 5,064,416 A | 11/1991 | Newgard et al. | |
| 5,108,380 A | 4/1992 | Herlitze et al. | |
| 5,330,435 A | 7/1994 | Vaillancourt | |
| 5,405,323 A | 4/1995 | Rogers et al. | |
| 5,456,675 A | 10/1995 | Wolbring et al. | |
| 5,613,663 A | 3/1997 | Schmidt et al. | |
| 5,749,857 A | 5/1998 | Cuppy | |
| 5,755,709 A | 5/1998 | Cuppy | |
| 5,817,069 A | 10/1998 | Arnett | |
| 5,954,698 A | 9/1999 | Pike | |
| 5,967,490 A | 10/1999 | Pike | |
| 5,984,895 A * | 11/1999 | Padilla et al. ............ | 604/168.01 |
| 6,699,221 B2 | 3/2004 | Vaillancourt | |
| 7,008,404 B2 | 3/2006 | Nakajima | |
| 2002/0183632 A1* | 12/2002 | Krivitski et al. .............. | 600/505 |
| 2003/0073976 A1 | 4/2003 | Brushey | |
| 2004/0158208 A1 | 8/2004 | Hiejima | |
| 2005/0015071 A1* | 1/2005 | Brimhall ....................... | 604/506 |
| 2006/0155245 A1 | 7/2006 | Woehr | |

FOREIGN PATENT DOCUMENTS

CA 1290213 C 10/1991
EP 0200393 A1 4/1986

* cited by examiner

Primary Examiner — Nicholas D Lucchesi
Assistant Examiner — Pritesh Patel
(74) Attorney, Agent, or Firm — Mony R. Ghose; Kirton & McConkie

(57) ABSTRACT

An extravascular system for accessing the vasculature of a patient may include a catheter assembly and an internal construct within the catheter assembly. At least one fluid flow space may exist between the internal construct and the catheter assembly.

22 Claims, 11 Drawing Sheets

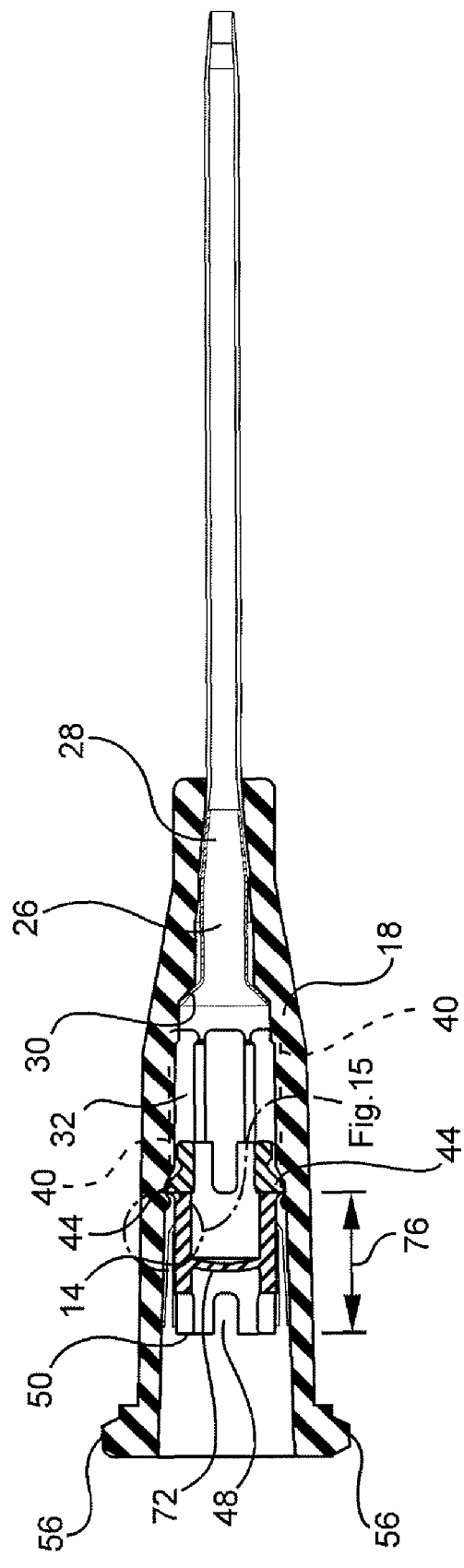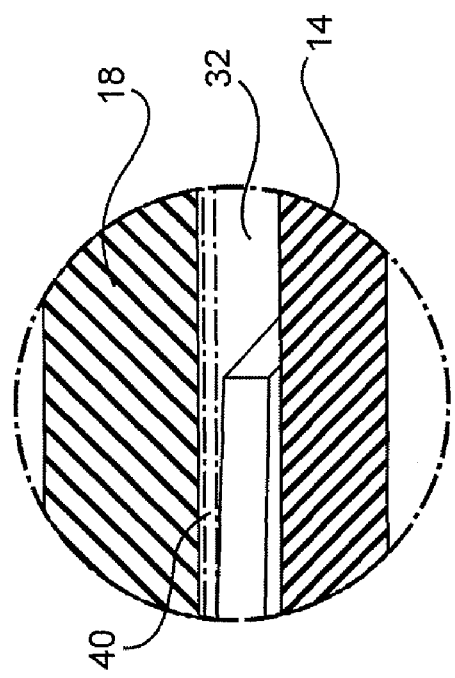
FIG. 14
FIG. 15

CONTROLLED FLASHBACK FOR VASCULAR ACCESS DEVICES

RELATED APPLICATIONS

This application claims the benefit of U.S. Provisional Application No. 60/777,841, filed Mar. 1, 2006, entitled SINGLE SEPTA VALVE DESIGN, and is incorporated herein.

BACKGROUND OF THE INVENTION

This invention relates generally to vascular access devices and methods, including catheter assemblies and devices used with catheter assemblies. Generally, vascular access devices are used for communicating fluid with the vascular system of patients. For example, catheters are used for infusing fluid, such as normal saline solution, various medicaments, and total parenteral nutrition, into a patient, withdrawing blood from a patient, or monitoring various parameters of the patient's vascular system.

A common type of intravenous (IV) catheter is an over-the-needle peripheral IV catheter. As its name implies, an over-the-needle catheter is mounted over an introducer needle having a sharp distal tip. At least the inner surface of the distal portion of the catheter tightly engages the outer surface of the needle to prevent peelback of the catheter and thus facilitate insertion of the catheter into the blood vessel. The catheter and the introducer needle are assembled so that the distal tip of the introducer needle extends beyond the distal tip of the catheter with the bevel of the needle facing up away from the patient's skin. The catheter and introducer needle are generally inserted at a shallow angle through the patient's skin into a blood vessel.

In order to verify proper placement of the needle and/or catheter in the blood vessel, the clinician generally confirms that there is "flashback", or flow, of blood into a flashback chamber of the catheter assembly. Once proper placement of the catheter into the blood vessel is confirmed, the clinician may apply pressure to the blood vessel by pressing down on the patient's skin over the blood vessel distal of the introducer needle and the catheter. This finger pressure occludes the vessel, minimizing further blood flow through the introducer needle and the catheter.

The clinician may then withdraw the introducer needle from the catheter. The introducer needle may be withdrawn into a needle shield device that covers the needle tip and prevents accidental needle sticks. In general, a needle shield includes a housing, a sleeve, or other similar device that is designed such that when the needle is withdrawn from the patient, the needle tip will be trapped/captured within the needle shield. The purpose of these needle shield devices is to house the tip of the needle in a secure location, thereby avoiding the possibility of needle sticks.

The needle and needle shield device, if used with the needle, are then separated from the catheter, which is left in place to provide intravenous access to the patient. Other vascular access devices may then access the catheter in order to continue patient treatment. During the entire period of catheter use, systems and methods are needed to continuously verify and maintain the proper vascular access device position within the vasculature of a patient.

BRIEF SUMMARY OF THE INVENTION

The present invention has been developed in response to problems and needs in the art that have not yet been fully resolved by currently available vascular access systems and methods. Thus, these systems and methods are developed to provide more efficient vascular access systems and methods capable of controlling the rate, location, duration, visualization, and/or other parameters of blood flow through a vascular access device and/or providing continuous verification of proper vascular access device position within the vasculature of a patient.

An extravascular system for accessing the vasculature of a patient may include a catheter assembly and an internal construct within the catheter assembly. The catheter assembly may include a catheter housing and a catheter tubing secured to the catheter housing. The catheter housing may include an internal surface. The internal construct may be at least partially housed within the catheter assembly. The internal construct may include an external surface.

At least one flow groove may exist between the internal surface of the catheter housing and the external surface of the internal construct. At least one ridge may exist adjacent the at least one flow groove and between the internal surface of the catheter housing and the external surface of the internal construct. The at least one ridge may vary in height, and the at least one flow groove may vary in depth. The at least one flow groove may extend along the entire length of the internal construct. The at least one flow groove may include at least six flow grooves, and the at least one ridge may include at least six ridges.

The system may also include a retention construct and a corresponding retention structure in communication with the catheter assembly and the internal construct. The retention construct and the corresponding retention structure are capable of at least temporarily retaining the internal construct in a position relative to the catheter assembly. The corresponding retention structure may include a retention space that permits fluid to flow past the retention construct when the retention construct is engaged with the corresponding retention structure.

The internal construct may be a septum, and the septum may have a septal disk. The system may also include a tapered wedge. The catheter tubing may be secured to the catheter housing with the tapered wedge.

Various separate vascular access devices may be employed with the catheter assembly. The internal construct may be positioned within the catheter housing to accommodate for various lengths of separate vascular access devices that may be employed with the catheter assembly. The catheter assembly may be formed of at least a semi-transparent material.

A method of optimizing the fluid flow parameters of an extravascular system used to infuse fluids and/or to withdraw blood for testing, donation, or other use may include providing a catheter assembly having a catheter tubing and a catheter housing and providing an internal construct within the catheter housing. The internal construct may be disposed within the catheter housing such that blood is allowed to flow between the internal construct and the catheter housing. The method may further include determining a first fluid flow rate through the catheter housing and determining a second fluid flow rate through the catheter tubing. Determining the first fluid flow rate may include determining the rate at which blood flows between the internal construct and the catheter housing. Determining the second fluid flow rate may include estimating a rate at which blood would flow through the catheter housing in the absence of the internal construct. The method may additionally include ensuring that the first fluid flow rate is greater than the second fluid flow rate. Ensuring that the first fluid flow rate is greater than the second fluid flow rate may include varying the first fluid flow rate.

Determining the first fluid flow rate may include calculating the flow (Q) using the following equation.

$$Q = \frac{\pi \cdot deq^4 \cdot (P3 - P2)}{128 \cdot \mu \cdot L \cdot K3\_2}$$

Determining the second fluid flow rate may include estimating a flow ($Q_c$) that would exist in the absence of the internal construct using the following equation.

$$Q_c = \frac{\pi (d1)^4 \cdot (P3 - P1)}{128 \cdot \mu \cdot L1\_2 \cdot K1\_2}$$

An extravascular system for accessing the vasculature of a patient may include means for accessing the vascular system of a patient, means for controlling fluid flow, and/or means for channeling fluid. The means for accessing the vascular system of a patient allows fluid flow therethrough. The means for controlling fluid flow is at least partially housed within the means for accessing the vascular system of a patient. And the means for channeling fluid may direct or channel fluid between the means for controlling fluid flow and the means for accessing the vascular system of a patient.

The system may also include means for at least temporarily retaining the means for controlling fluid flow in a position relative to the means for accessing the vascular system of a patient. The means for channeling fluid is capable of channeling fluid past the means for at least temporarily retaining. The system may also include means for accommodating various lengths of separate vascular access devices that may be employed with the means for accessing the vascular system of a patient.

A method of optimizing the fluid flow parameters of an extravascular system used to access an extravascular system of a patient is also provided. The method may include providing a catheter assembly having a catheter tubing and a catheter housing and providing an internal construct within the catheter housing such that blood is allowed to flow between the internal construct and the catheter housing. The method may further include determining a first fluid flow rate through the catheter housing, such as by determining the rate at which blood flows between the internal construct and the catheter housing. Additionally, the method may include determining a second fluid flow rate through the catheter tubing, such as by estimating a rate at which blood would flow through the catheter housing in the absence of the internal construct. Moreover, the method may include disposing the internal construct within the catheter housing in a first configuration such that blood is metered to flow between the internal construct and the catheter housing at a first fluid flow rate less than the second fluid flow rate. The method may additionally include associating the internal construct and the catheter housing to provide at least one indwelling configuration and each of the indwelling configurations may provide a customized first fluid flow rate, which may be greater or less than the second fluid flow rate.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

FIG. 14 is a cross section view of a catheter housing and a septum within the catheter housing.

FIG. 15 is a close-up cross section view of a portion of the septum and catheter housing of FIG. 14.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
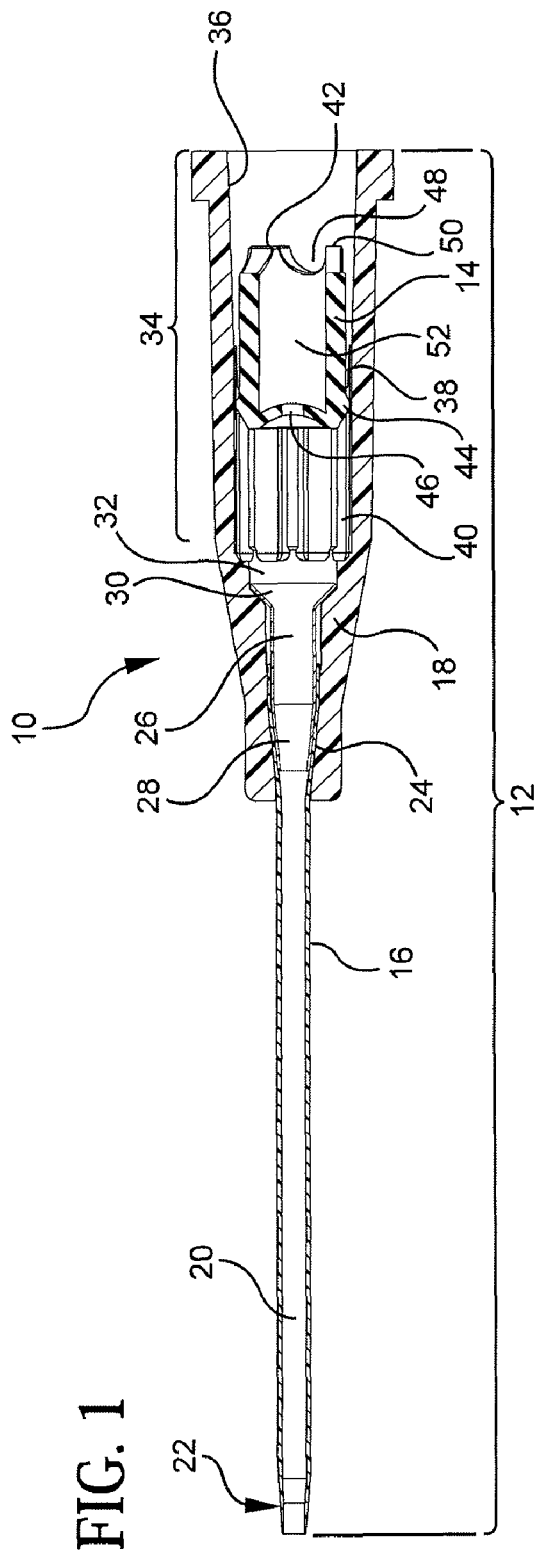
FIG. 1 is a cross section view of an extravascular system.
Figure 2:
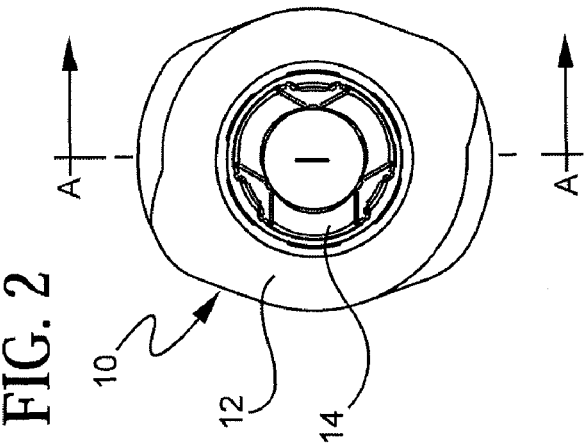
FIG. 2 is a proximal end view of the extravascular system of FIG. 1.

Referring to FIG. 1, a cross section view of an extravascular system 10 shows a vascular access device such as a catheter assembly 12 having an internal construct such as a septum 14 at least partially housed within the catheter assembly 12. The cross section view of the extravascular system 10 of FIG. 1 is a view taken along lines A-A of FIG. 2. FIG. 2 is a proximal end view of the extravascular system 10 revealing the internal construct or septum 14 housed within the catheter assembly 12.

Referring collectively to FIGS. 1 and 2, the catheter assembly 12 includes an insertion portion such as a catheter tubing 16 secured to the distal internal end of a catheter housing 18. The catheter tubing 16 includes a lumen 20 through which a needle may be inserted in order to access the vasculature of a patient. At its distal tip 22, the catheter tubing 16 forms a taper that narrows towards the point of the distal tip of a needle that may be inserted within the catheter tubing 16. The tapered tip 22 is formed in order to enable the tip 22 of the catheter tubing 16 to easily penetrate the tissue of a patient through which the needle and catheter tubing 16 are inserted. Ultimately, the tapered tip 22 of the catheter tubing will be advanced into the vasculature of a patient and the needle will be withdrawn from the catheter tubing 16.

The proximal end of the catheter tubing 16 expands to form an increased diameter and cross section 24 as the catheter tubing 16 enters an internal lumen of the distal end of the catheter housing 18. The portion of the catheter tubing 16 with the expanded diameter 24 is tapered such that the catheter tubing 16 will not easily separate from the corresponding tapered internal lumen of the distal portion of the catheter housing 18. To provide additional security capable of maintaining the position of the catheter tubing 16 within the catheter housing 18, a wedge 26 may be placed within the internal lumen of the distal end of the catheter housing 18 and against the interior surface of the expanded portion 24 of the catheter tubing 16. The wedge 26 functions at least in part to force the expanded portion 24 of the catheter tubing 16 against the internal surface of the distal portion of the catheter housing 18. By forcing the material of the expanded portion 24 against the internal surface of the distal portion of the catheter housing 18, the wedge 26 ensures that the catheter tubing 16 remains securely connected to the catheter housing 18.

In addition, the wedge 26 also provides a tapered lumen 28 within the wedge 26 at the distal portion of the wedge 26. The wedge 26 also includes a tapered lumen 30 at its proximal end. The tapered lumen 28 of the wedge 26 further serves to secure the catheter tubing 16 to the catheter housing 18. In addition, the tapered lumen 28 serves to guide the distal tip of a needle through the narrowing lumen of the extravascular system 10 towards the distal portion of the extravascular system 10. Tapered lumen 30 of wedge 26 provides a similar function as the tapered lumen 28, in that the tapered lumen 30 provides a further guided narrowing of the lumen of the extravascular system 10 through which the tip of a needle may travel in order to reach its temporary destination at the distal end of the extravascular system 10. Tapered lumen 30 provides guidance and protection capable of ensuring that the tip of the needle does not stick against any internal surfaces of the housing 18 as the tip of the needle is advanced through the lumen of the extravascular system 10. The internal surface of the wedge 26 may be a low friction surface or any other type of surface capable of successfully guiding the sharp point of the tip of a needle through a lumen of, for example, a progressively narrowing diameter without permitting the point of the tip of the needle to stick into any surface of the wedge 26.

Preferably, the wedge 26, catheter tubing 16, housing 18, and septum 14 of the extravascular system 10 will be formed of a transparent material. The transparent, or semi-transparent properties of the materials of the extravascular system 10 will enable a clinician or other user of the extravascular system 10 to visualize the flow of blood and/or other liquids in addition to the operation of internal components such as the internal construct or septum 14 and/or the tip or other portions of a needle as such internal components move within the interior of the catheter assembly 12. A clinician or operator of the extravascular system 10 who is able to visualize the internal environment and operations of the catheter assembly 12 will be able to operate the extravascular system 10 more effectively.

At the proximal tapered end 30 of the wedge 26, the internal lumen 32 of the catheter housing 18 broadens to form a chamber large enough to house a movable internal construct such as the septum 14 along a length of the lumen 32 which is greater than the total length of the septum 14. The chamber may be formed as a barrel 34 that includes an internal diameter that corresponds with an external diameter of the septum 14, such that the external surface of the septum 14 communicates with the internal surface of the barrel 34. The barrel 34 may include a relatively smooth internal surface 36 at the proximal end of the catheter housing 18. As the barrel 34 continues from the relatively smooth surface 36 in a distal direction, the internal surface 36 of the barrel 34 may taper or narrow at a section 38 towards a more distal section of the barrel 34. The more distal section of the barrel 34 within the housing 18 will form one or more flow and/or flash grooves 40 within the internal surface of the barrel 34, housing 18, and/or the external surface of the septum 14. The flow grooves 40 form channels through which fluid may travel between an internal surface of the catheter housing 18 and an external surface of the septum 14.

The barrel 34 may include a length that is greater than the length of the septum 14. Preferably, the barrel 34, and flash grooves 40 within the barrel 34, will include a length great enough to accommodate a variety of depths that may be penetrated by a variety of tips of vascular access devices that will be inserted into the lumen 32 of the catheter housing 18 in order to come into communication with the proximal end 42 of the septum 14. For example, a tip of a Luer access device may be inserted as a separate vascular access device into the proximal end of the catheter assembly 12 and may come into direct contact with the proximal end of the septum 14. The Luer tip may then force the septum 14 in a distal direction to a maximum depth. At the maximum depth, the Luer tip is unable to further advance the septum 14 in a distal direction within the lumen 32. The length of the barrel 34 and/or grooves 40 may be great enough to accommodate the maximum insertion depth of the septum 14 under the influence of any Luer tip. Conversely, Luer tips capable of only minimal depth insertion may be applied to advance the septum 14 only a minimal amount within the lumen 32 of the catheter housing 18. The length of the barrel 34 and/or flash grooves 40 may similarly accommodate this minimal insertion depth.

The septum 14 may be advanced from the proximal end of the internal lumen 32 of the catheter assembly 12 towards the distal end of the lumen 32 under the influence of a separate vascular access device which may be used in conjunction with or as a part of the extravascular system 10. The septum 14 may be advanced by exerting force upon the proximal end 42 of the septum 14. As the septum 14 advances through the internal lumen 32 from the proximal end of the lumen 32 towards the distal end of the lumen 32, the external surface of the septum 14 will come into contact with the internal surface of the lumen 32 as the lumen 32 internal surface tapers along section 38 towards the distal portion having the flow grooves 40.

The septum 14, and/or internal surface of the lumen 32, barrel 34, and/or housing 18, may include a retention construct or ring 44. For example, the retention ring 44 may be formed at the distal end of the septum 14 or along the length of the septum. The retention ring 44 is a formation of material along the external surface of the septum 14 capable of coming into greater or more intense contact with surfaces of the lumen 32, barrel 34, and/or housing 18. For example, as the septum 14 is advanced through the barrel 34 along the tapered section 38 and against the grooves 40, the retention ring 44 will be compressed by the ridges of the flow grooves 40, causing the septum 14 to reside in a relatively secure and relatively unmovable position within the barrel 34.

The septum 14 may include a slit 46 through which the point, tip, and cannula of a needle may penetrate and extend. The septum 14 may include other additional features which will be described in detail herein, including flow spaces 48 and ridges 50 at the proximal end 42 of the septum 14. The flow spaces 48 enable fluid to flow from the tip of a separate vascular access device into an interior chamber 52 of the septum 14 when the ridges 50 are in direct contact with at least one surface of the mating vascular access device.

Figure 3:
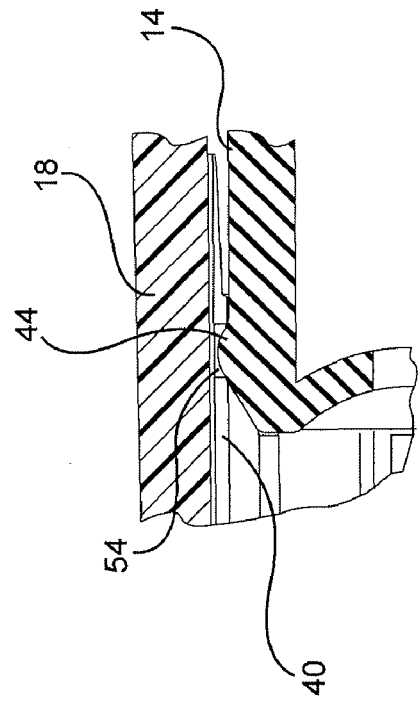
FIG. 3 is a close-up cross section view of a distal portion of the extravascular system of FIG. 1.

Referring to FIG. 3, a close-up cross section view of a distal portion of the septum 14 is shown housed within the catheter housing 18. The close-up view reveals the retention ring 44 retained by a corresponding retention structure or lack of structure, such as a retention space 54, that has been formed in order to temporarily retain the retention ring 44 within the retention space 54 until the septum 14 is moved by a separate vascular access device. Thus, the retention space 54 functions in cooperation with the retention ring 44 to ensure that the septum 14 remains located within its proper position after initial manufacturing assembly and prior to engagement with a separate vascular access device during operation of the extravascular system 10.

The flow grooves 40 are also shown within the close-up view of FIG. 3 extending from the distal end of the barrel 34 through the retention space 54 and beyond the retention ring 44 in a proximal direction. The flash grooves 40 thus permit the travel of fluid past the septum 14 in order to provide an operator of the extravascular system 10 with a visual confirmation of proper location of the tip 22 of the catheter tubing and/or the tip of a needle within the vasculature of a patient during operation of the extravascular system 10. The flash grooves 40 function to provide flashback confirmation of blood around the exterior surface of the septum 14 both while the retention ring 44 is lodged within the retention space 54 and after the retention ring 44 has advanced out of the retention space 54 and along the flash groove 40 portion of the barrel 34. Thus, the flash grooves 40 function to provide initial, secondary, and tertiary flashback during operation of the extravascular system 10 regardless of the location and/or depth of penetration of the septum 14 within the lumen 32.

Figure 4:
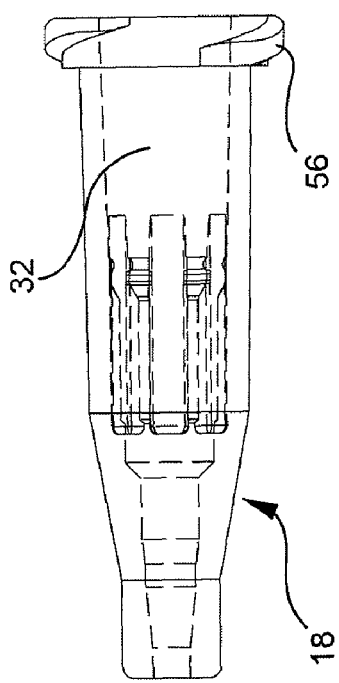
FIG. 4 is a side view of a catheter housing.

Referring to FIG. 4, a side view of the catheter housing 18 of the catheter assembly 12 is shown and will be described in greater detail. In addition to the features already described, the external surface of the catheter housing 18 may include one or more threads 56 or other means of attachment capable of securing the proximal portion of the catheter housing 18 to the distal portion or other portion of a mating vascular access device which may be used to access the internal lumen 32 of the catheter housing 18. The vascular access device will have corresponding male or female threads capable of engaging with the threads 56.

The transparent, semi-transparent, and/or translucent material of the catheter housing 18 reveals the interior structure of the catheter housing 18, as will be described in greater detail herein. The external diameter of the catheter housing 18 forms a narrowing taper from the proximal end of the catheter housing 18 as it advances towards the distal end of the catheter housing 18. The gradual, narrowing taper of the catheter housing 18 may exist as a result of the corresponding gradual and narrowing taper of the lumen 32 and other lumens within the catheter housing 18 as those lumens advance towards the distal end of the catheter housing 18. Since a uniform amount of material and/or structural stability may, in certain applications, be necessary or desirable to ensure proper operation of the catheter housing 18 and catheter assembly 12 along the length of the catheter housing 18, the catheter housing 18 may be narrowed as the internal lumens 32 are narrowed. In addition, narrowing the external diameter of the catheter housing 18 towards the distal tip of the catheter housing 18 will decrease the amount of material present at the insertion site within the tissue of a patient. Since an operator of the extravascular system 10 will need and/or prefer an unobstructed view and operation space at the site of needle and/or catheter tip 22 insertion, a decreased amount of material at the distal end of the catheter housing 18 is preferred.

Figure 5:
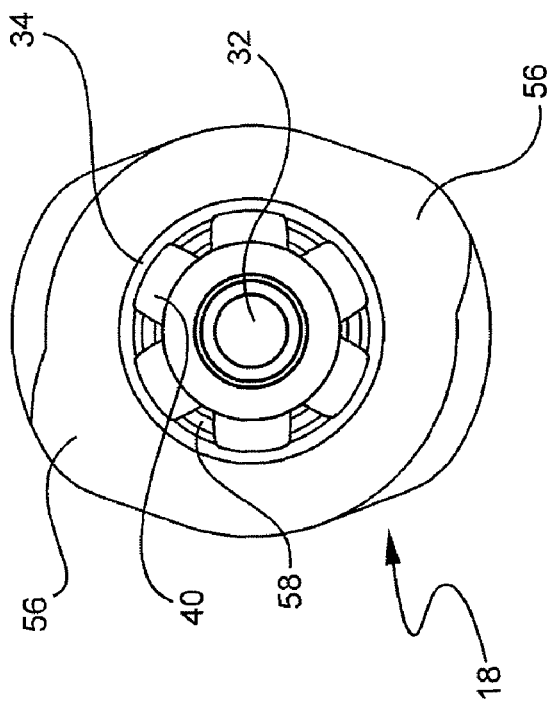
FIG. 5 is a proximal end view of the catheter housing of FIG. 4.

Referring to FIG. 5, a proximal end view of the catheter housing 18 of FIG. 4 is shown. The proximal end view reveals the threads 56 located on the exterior surface of the catheter housing 18, the lumen 32 extending through the axial center of the catheter housing 18, the internal surface of the barrel 34, and six flash grooves 40 formed between flash groove ridges 58 within the distal portion of the barrel 34. The six flash grooves 40 are uniformly spaced around the axial center of the catheter housing 18 in order to ensure uniform structural support, stability, and guidance with which the exterior surface of the septum 14 may communicate. By providing a uniform array of flash grooves 40 and corresponding flash groove ridges 58, a septum 14 or other internal construct may progress in a predictable, continuous manner towards the distal end of the lumen 32 of the catheter housing 18. Further, the uniform array of the flash grooves 40 and their corresponding flash groove ridges 58 may increase the ease of manufacturing the catheter housing 18. A number of manufacturing techniques known in the art may be used to manufacture the catheter housing 18. In the event that the flash grooves 40 are formed using a cutting process, two opposing flash grooves 40 may be cut at the same time since the two opposing flash grooves 40 are linearly aligned with each other.

Figure 6:
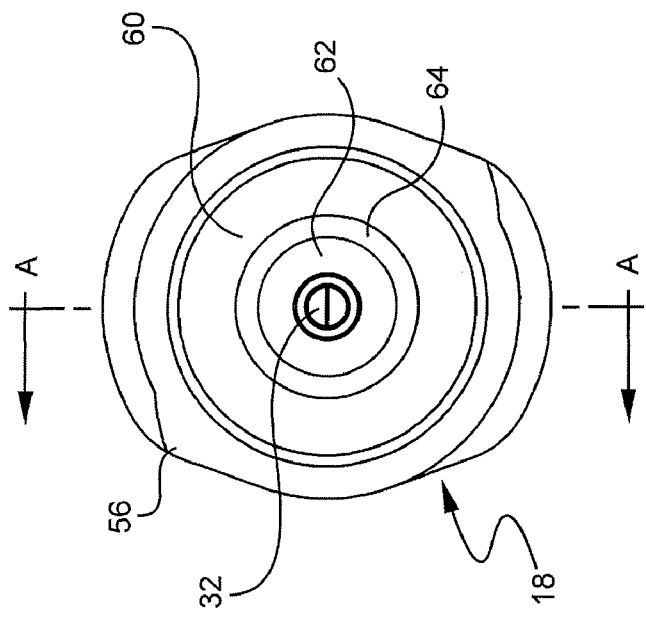
FIG. 6 is a distal end view of the catheter housing of FIG. 4.

Referring to FIG. 6, a distal end view of the catheter housing 18 of FIG. 4 is shown. The distal end view of the catheter housing 18 reveals the threads 56 on the external surface of the catheter housing 18, the tapering proximal end 60 of the catheter housing 18, a relatively blunt distal end 62 of the catheter housing 18 having a rounded edge 64, and the internal tapering lumen 32 through the axial center of the catheter housing 18.

Figure 7:
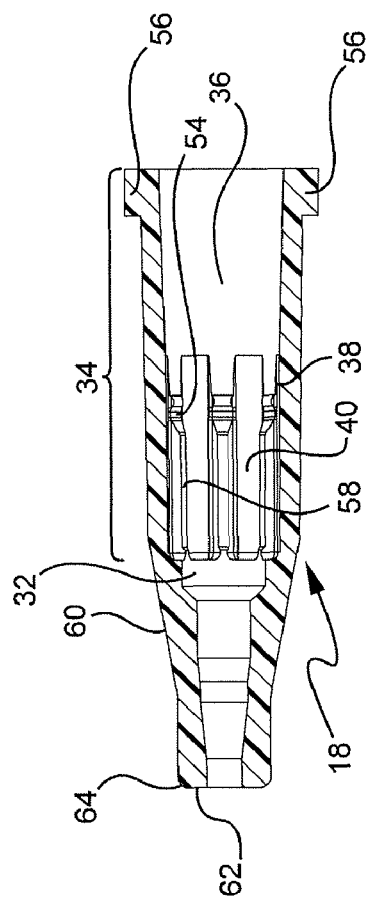
FIG. 7 is a cross section view of the catheter housing of FIGS. 4 through 6, taken along lines A-A of FIG. 6.

Referring to FIG. 7, a cross section view of the catheter housing 18 of FIGS. 4 through 6 is shown taken along lines A-A of FIG. 6. The cross section view of the catheter housing 18 reveals the relatively blunt distal end 62 having a rounded edge 64, an external tapered section 60 of the distal end of the catheter housing 18, a generally tapered external portion corresponding to the barrel 34, and the external threads 56 along the external portion of the catheter housing 18. Along the internal surfaces of the catheter housing 18, the cross section view reveals a generally tapered and smooth proximal internal surface 36 narrowing its diameter as the internal surface 36 travels from the proximal end of the housing 18 towards the tapered section 38. The internal surface 36 further narrows its diameter as it travels along the grooves 40, in a distal direction, towards the retention space 54. The interior surface 36 may be formed, for example, as a six percent female Luer conical fitting according to ISO standard 594-1. The interior surface 36 may be formed in order to accommodate any of a variety of male Luer tips.

A retention space 54 is formed within each ridge 58. Each ridge 58 separates one flash groove 40 from another flash groove 40. The ridges 58 increase in height just distal from the retention spaces 54 and between the retention spaces 54 and the distally-located remainder of the narrowing lumen 32. The retention spaces 54 are not as deep as the grooves 40. That is, the grooves 40 cut deeper into the material of the catheter housing 18 than the retention spaces 54. Thus, when the retention ring 44 is housed within the retention spaces 54, there is still adequate space within each groove 40 between the outer surface of the retention ring 44 and the inner surface of the catheter housing 18 through which fluid may pass.

The limited amount of space between the retention ring 44 and the surface of the catheter housing 18 permits a controlled amount of flashback to occur during operation of the extravascular system 10 while the septum 14 is positioned within the retention spaces 54. After the septum 14 is advanced distally, such that the retention ring 44 is moved from the retention spaces 54 to the tops of the ridges 58, the space between the outer surface of the retention ring 44 and the inner surface of the catheter housing 18 will increase as the volume of the flash grooves 40 also increases.

As the volume of the flash grooves 40 increases, a greater amount of fluid will be permitted to flow between the septum 14 and the interior surface of the catheter housing 18. This increased amount of fluid flow may be controlled and/or used by an operator and/or clinician of the extravascular system 10 in order to monitor and/or adjust the positioning of a needle and/or catheter 12 tip within the vasculature of a patient. As shown in FIG. 7, the flashback volume within the flashback grooves 40 will increase after the septum 14 is engaged by the tip of a separate vascular access device. However, the flashback volume within any flashback chamber and/or space such as the flashback grooves 40 may increase, decrease, and/or remain constant depending upon the particular use and/or configuration of the components of the extravascular system 10. For example, the opposite of that shown in FIG. 7 may be provided such that once the septum 14 is engaged by the tip of a separate access device, the retention ring 44 may move from a position of greater flashback volume to a position of lesser flashback volume as the corresponding flash grooves 40 decrease in volume.

In some implementations of the systems and methods of the present disclosure, the extravascular system 10 may include a catheter assembly and an internal construct associated so as to provide at least two configurations. For example, the extravascular system may provide one or more insertion configurations and one or more indwelling configurations. In some implementations, one of the insertion configurations may correspond to the configuration having the retention ring 44 disposed in the retention space 54. Similarly, one or more of the indwelling configurations may be provided by the configurations wherein the internal construct 14 is moved distally and the retention ring 44 is supported on the flash ridges 58. As discussed above, depending on the intended usage of the extravascular system 10, the relative flow rates permitted in the various configurations may be selected to provide the desired functionality. For example, the flow rate may be greater or lesser in an insertion configuration and/or in an indwelling configuration. Additional discussion of flow rates in different configurations and methods of configuring the catheter assembly and the internal construct to provide the desired flow rates are discussed in greater detail below.

Figure 8:
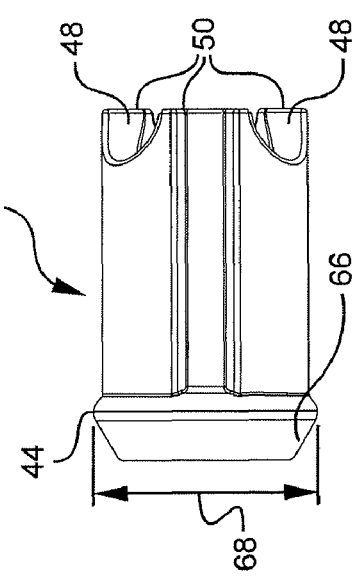
FIG. 8 is a side view of a septum.

Referring to FIG. 8, a side view of the septum 14 is shown. The septum 14 includes a tapered conical nose 66 at its distal end adjacent the retention ring 44. The retention ring 44 provides the greatest diameter 68 of the septum 14. The septum 14 forms a generally cylindrical shape and includes at least one flow space 48 and contact surface 50 at the proximal end of the septum 14.

Figure 9:
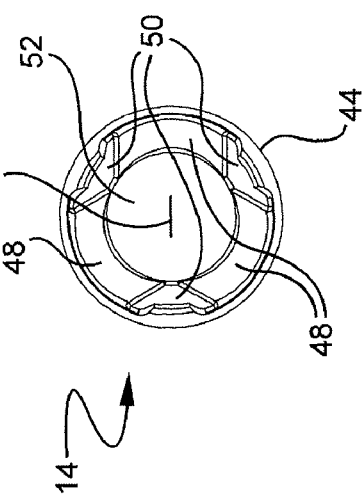
FIG. 9 is a proximal end view of the septum of FIG. 8.

Referring to FIG. 9, a proximal end view of the septum 14 of FIG. 8 is shown. The proximal end view illustrates the internal view of the slit 70 through which the point, tip, and/or cannula of a needle may extend. The slit 70 may be formed after molding the septum 14 and is seen in FIG. 9 through the internal chamber 52 of the septum 14. The proximal end view of the septum 14 also reveals the retention ring 44 forming the outer most surface along the circumference of the septum 14. The proximal end view also reveals three contact surfaces 50 separated by three corresponding flow spaces 48.

Figure 10:
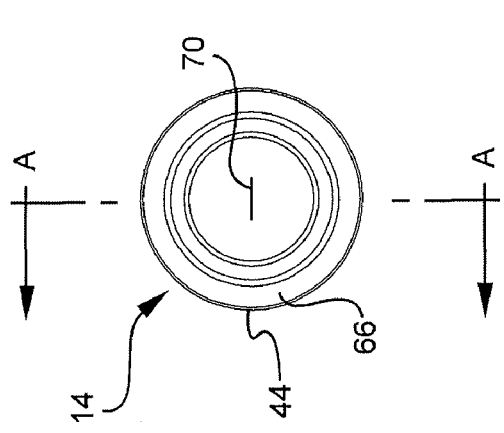
FIG. 10 is a distal end view of the septum of FIG. 8.

Referring to FIG. 10, a distal end view of the septum 14 of FIG. 8 is shown. The distal end view reveals the distal surface of the slit 70 cut across the axial center of the septum 14. The distal end view also reveals the tapered nose 66 tapering towards the increased diameter of the retention ring 44. The retention ring 44 forms the outer most circumferential surface of the septum 14.

Figure 11:
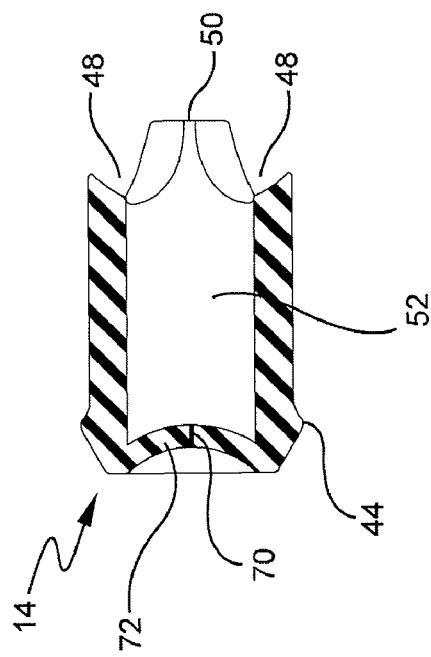
FIG. 11 is a cross section view of the septum of FIGS. 8 through 10, taken along lines A-A of FIG. 10.

Referring to FIG. 11, the septum 14 of FIGS. 8 through 10 is shown in cross section view taken along lines A-A of FIG. 10. The cross section view of the septum 14 reveals the slit 70 cut, molded, or otherwise formed through a septal disk 72. The septal disk 72 forms a barrier capable of sealing fluid from without the internal chamber 52 of the septum 14 from the space within the internal chamber 52. The disk 72 and slit 70 function to permit the passage of a needle through the slit 70 while limiting the passage of any fluid between the external surface of the needle and the internal surface of slit 70 of the disk 72.

In one embodiment, the materials, dimensions, and/or orientations of the slit 70 and/or disk 72 may be modified in order to permit a certain amount of fluid flow between the external surface of a needle and the internal surface of the slit 70 when a needle is extending through the slit 70. For example, a simple straight cut slit such as that shown in FIG. 9 may in certain septal disks 72 having certain material properties permit a triangular shaped space on either end of the slit 70 to exist when a needle is extending through the slit 70. Fluid such as blood and/or other infusate fluid may be transferred through the triangular shaped spaces between the needle and the ends of the slit 70.

Such spaces may be preferable depending upon the desired use of the extravascular system 10 in order to provide blood flashback and/or other fluid communication helpful to the operation of the system 10. However, such spaces may not be desired, for example where an operator of the system 10 desires to view the passage of all fluid within the extravascular system 10 and there are fluid routes alternate to the spaces. In examples where the septum 14 is formed of a material that is either not transparent or is difficult to see through, an operator wishing to visualize all fluid flow within the extravascular system 10 will prefer a system fluid travels only through visible fluid routes. For example, a system where the slit 70 seals entirely around the outer surface of the cannula of a needle such that no fluid may pass through the slit 70 and into the internal chamber 52 may advantageously require all fluid to pass around the exterior surface of the septum 14, past the retention ring 44, and between the exterior surface of the septum 14 and the interior surface of the transparent catheter housing 18.

The cross section of FIG. 11 also partially illustrates two of the three flow spaces 48 separated from each other by a single contact surface 50. As previously described, the contact surfaces 50 form a platform against which the tip of a male Luer or other structure of another vascular access device may be contacted. When the tip of a male Luer contacts the contact surfaces 50, the tip may exert force against the contact surfaces 50 in order to advance the septum 14 in a distal direction within the lumen 32 of the catheter assembly 12. If the proximal portion of the septum 14 included a continuous contact surface 50 for a tip of a male Luer to contact, any fluid transferred from within the lumen of the male Luer tip would be forced directly into, rather than around, the internal chamber 52 of the septum 14.

Because the septal disk 72 is formed to be concave towards the proximal direction of the internal chamber 52, after the needle has been withdrawn from the slit 70, the slit 70 will become closed and sealed to fluid transfer. With the slit 70 closed within the convex septal disk 72, no fluid will be permitted to escape the internal chamber 52 of the septum 14. Thus, the purpose of an extravascular system 10 that enables fluid to be infused into the vascular system of a patient would be thwarted in such a system having a continuous contact surface 50 on the proximal portion of the septum 14. Thus, to alleviate the fluid barrier that would otherwise exist, the flow spaces 48 have been cut, molded, or otherwise formed within the proximal portion of the septum 14.

The fluid flow spaces 48 permit fluid to flow from within the lumen of a tip of a male Luer or other vascular access device into the internal chamber 52, then from the internal chamber 52 through the fluid flow spaces 48, and ultimately from the fluid flow spaces 48 distally around the external surface of the septum 14 within grooves formed on either the exterior surface of the septum 14 and/or the internal surface of the catheter housing 18, such as the grooves 40. Any number of flow spaces 48 and/or contact surfaces 50 may be formed in order to achieve the objective of providing a contact surface against which an additional vascular access device may contact and providing a means of flowing fluid through the extravascular system 10 into the vasculature of a patient. The flow spaces 48 may also vary in location. For example, the flow spaces 48 may be formed as holes through the center, midway between the proximal and distal ends of the septum 14, such that fluid may flow into the chamber 52, through the flow spaces 48, and on towards the vasculature of a patient.

Figure 12:
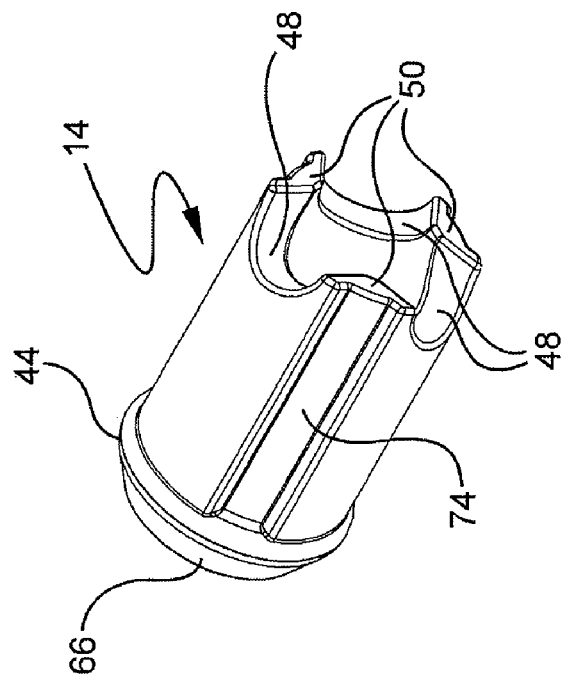
FIG. 12 is a perspective view of the side and proximal end of the septum of FIG. 8.

Referring to FIG. 12, a perspective view of the side and proximal end of the septum 14 is shown. The proximal view reveals the three contact surfaces 50 and the three corresponding flow channels 48, the tapered end 66, and the retention ring 44. In addition, the outer surface of the septum 14 includes at least one flow channel or flow groove 74 through which fluid may travel. The at least one flow groove 74 is formed to originate at each of the contact surfaces 50 in the proximal end of the septum 14 and terminate at the retention ring 44. In certain embodiments, the flow grooves 74 may extend through the retention ring 44. The flow grooves 74 may be formed for purposes similar to the flow grooves 40, that is, at least to provide fluid travel between the exterior surface of the septum 14 and the interior surface of the catheter housing 18.

Figure 13:
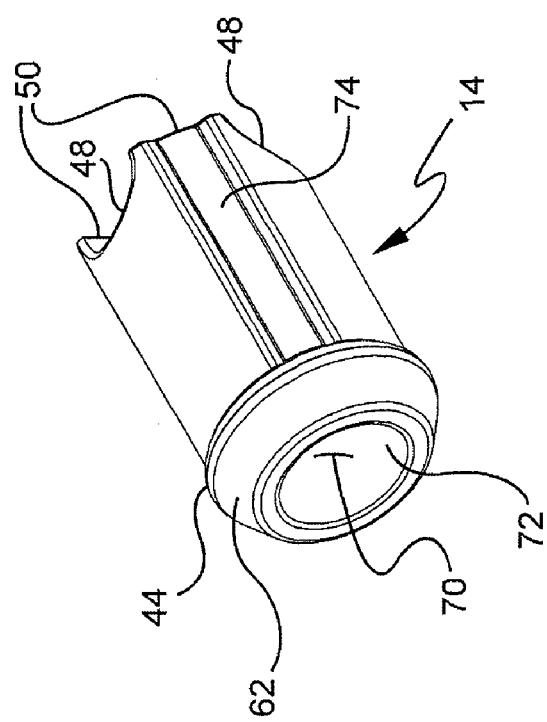
FIG. 13 is a perspective view of the side and distal end of the septum of FIG. 8.

Referring to FIG. 13, a perspective view of the septum 14 illustrates the side and distal portions of the septum 14. The perspective view illustrates the slit 70 within the disk 72, the disk 72 surrounded by the tapered surface 66, the tapered surface 66 adjacent the retention ring 44, the at least one flow groove 74 terminating at the retention ring 44 and originating at a contact surface 50, and the flow spaces 48 separated by the contact surfaces 50. The septal disk 72 of the septum 14 described with reference to FIGS. 8 through 13 is formed at the distal end of the septum 14. However, the septal disk 72 may be formed along any portion of the length of the internal space 52 of the septum 14. Further, various other configurations, features, structures, and/or orientations of the features of the septum 14 may be modified depending on the preferred use of an extravascular system 10, as will be described and shown in another example of a septum in the following drawings.

Referring to FIG. 14, a cross section view of an alternate embodiment of a catheter housing 18 and a septum 14 is shown. The catheter housing 18 may house a wedge 26 having a distal taper 28 and a proximal taper 30. The catheter housing 18 may also form threads 56 on its proximal external portion capable of engaging with corresponding threads on an additional vascular access device. The additional vascular access device may be inserted into the proximal end of the catheter housing 18 in order to come into contact with one or more contact surfaces 50 and advance the septum 14 distally within an internal lumen 32 of the catheter housing 18. As the septum 14 advances distally through the lumen 32, the volume within flash grooves 40 may increase between the exterior surface of a retention ring 44 of the septum 14 and an interior surface of the catheter housing 18, as will be described in greater detail with reference to FIG. 15.

Referring to FIG. 15, a close-up cross section view of a portion of the septum 14 and catheter housing 18 is shown. The close-up cross section view illustrates that the depth of a groove 40 increases as the groove 40 advances distally along the internal lumen 32 of the catheter housing 18. The grooves 40 of varying depth along the lumen 32 provide an environment that may be manipulated by an operator of the extravascular system 10 to which the catheter housing 18 may form part, in order to control the rate of flashback within the grooves 40.

For example, an operator of the extravascular system 10 desiring a minimal flashback rate may advance the septum 14 in a distal direction within the lumen 32 to a minimal distance, such that the outer surface of the septum 14 such as the retention ring 44 is in contact with the ridges 58 between the grooves 40 at a point where the grooves 40 have a minimum depth. At a minimum depth, the grooves 40 will only permit a minimum amount of fluid communication and/or blood flashback to travel through the grooves 40, between the outer surface of the septum 14 and the inner surface of the catheter housing 18. Conversely, an operator who desires a maximum rate of fluid flow and/or blood flashback will advance the septum 14 through the lumen 32 to a point at which the exterior surface of the septum 14 corresponds with a maximum depth in the flow grooves 40.

Returning to FIG. 14, the septum 14 is shown within the lumen 32 having been advanced to a maximum flow groove 40 depth, such that fluid will flow and/or blood will flashback within the grooves 40 and between the exterior surface of the retention ring 44 and the interior surface of the catheter housing 18 at a maximum flow rate. The maximum depth of the grooves 40 exists both in the location shown that corresponds with the retention ring 44 and at any point distal therefrom. The space between the current location of the septum 14 and the maximum insertion location of the septum 14 within the lumen 32 of FIG. 14 illustrates a distance 76 which compensates for and accommodates the differences in various Luer lengths that may be employed in conjunction with the catheter assembly 12 described with reference to FIG. 14. The distance compensation 76 has been discussed previously with reference to the embodiment illustrated in FIGS. 1 through 7.

Figure 16:
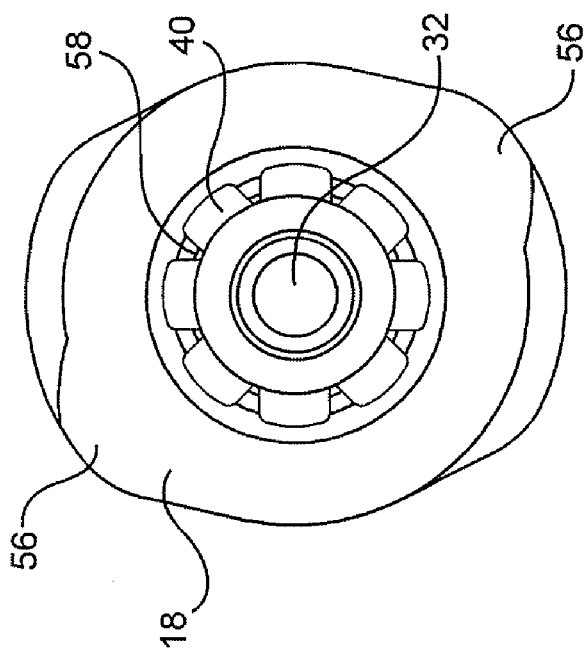
FIG. 16 is a proximal end view of the catheter housing and septum of FIG. 14.

Referring to FIG. 16, a proximal end view of the catheter housing 18 and septum 14 is shown. The proximal end view reveals the threads 56 on the external surface of the catheter housing 18. The septum 14 is shown housed within the lumen 32 of the catheter housing 18. The septum 14 reveals four contact surfaces 50 separating four corresponding flow spaces 48. The lumen 32 also includes eight flow grooves 40 forming a volume between the exterior surface of the septum 14 and the interior surface of the lumen 32 of the catheter housing 18.

Figure 17:
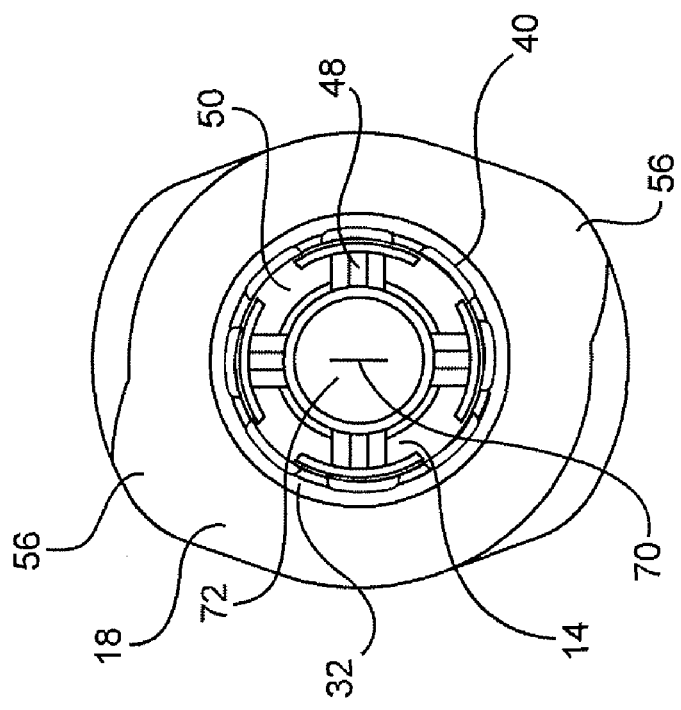
FIG. 17 is a proximal end view of the catheter housing of FIG. 14 without the septum.

Referring to FIG. 17, a proximal view of the catheter housing 18 without the septum 14 is shown. The proximal view reveals the lumen 32 extending through the axial center of the housing 18. Eight flow channels 40 are uniformly spaced around the axial center of the housing 18 by neighboring flow channel ridges 58.

Figure 18:
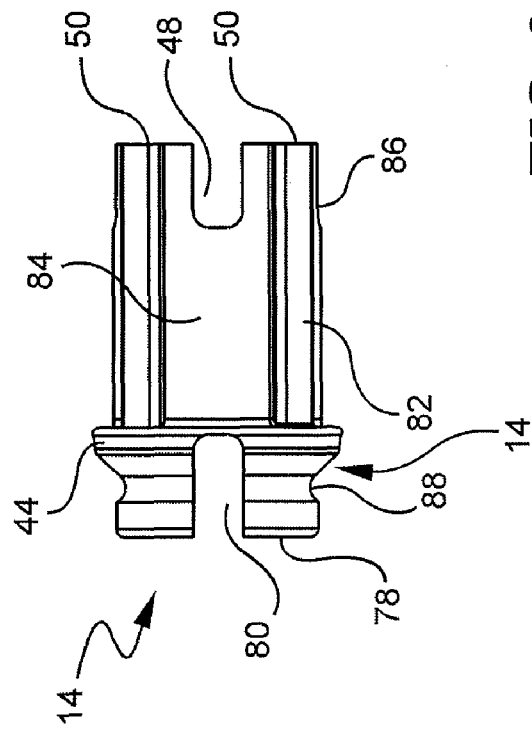
FIG. 18 is a side view of a septum.

Referring to FIG. 18, a side view of the septum 14 described with reference to FIGS. 14 through 16 is shown. The side view of the septum 14 reveals a tapered distal end 78 having four flow channels 80 formed therein, a retention ring 44 forming the largest diameter of the septum 14, a body 82 including four wide flow channels 84, and a proximal end 86 including four flow channels 48 and four contact surfaces 50. The distal end 78 of the septum 14 may include a flow ring 88 formed around its circumference in order to promote the distribution of fluids from one flow channel 80 to another flow channel 80. Thus, the septum 14 described with reference to FIG. 18 includes multiple flow channels, rings, and/or grooves 80, 88, 84, and/or 48 capable of facilitating the communication of fluid into and around the exterior surface of the septum 14. Fluid is able to travel through these grooves in between surfaces of the septum 14 and/or surfaces of the catheter housing 18.

Figure 19:
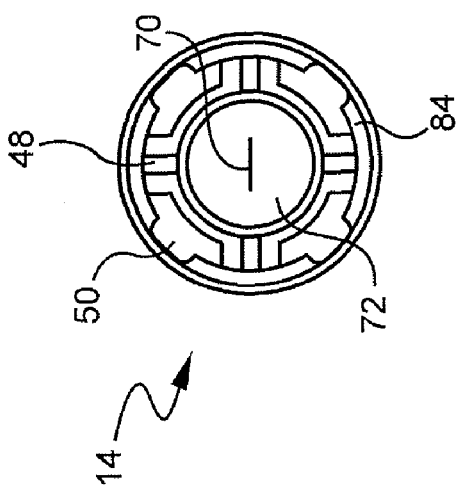
FIG. 19 is a proximal end view of the septum of FIG. 18.

Referring now to FIG. 19, a proximal end view of the septum 14 of FIG. 18 is shown. The proximal end view illustrates the proximal surface of a slit 70 formed through a septal disk 72. The proximal view also illustrates four contact surfaces 50 separating four flow spaces 48 and four flow channels 84 from each other.

Figure 20:
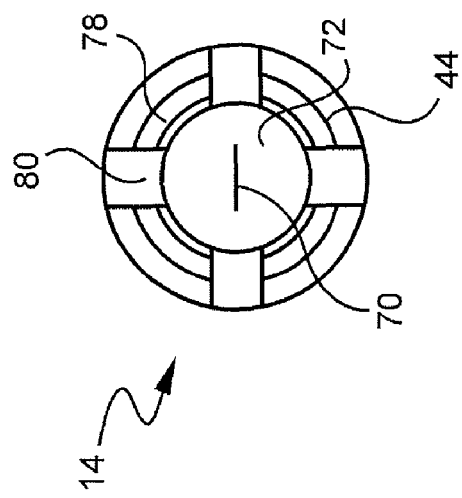
FIG. 20 is a distal end view of the septum of FIG. 18.

Referring to FIG. 20, a distal end view of the septum 14 described with reference to FIGS. 18 and 19 is shown. In the distal end view, the distal surface of the slit 70 formed within the disk 72 is shown. Also shown are four distal contact surfaces 78 separating four distal flow spaces 80. The four distal flow spaces 80 are formed both within the distal end 78 and at least a portion of the retention ring 44.

Figure 21:
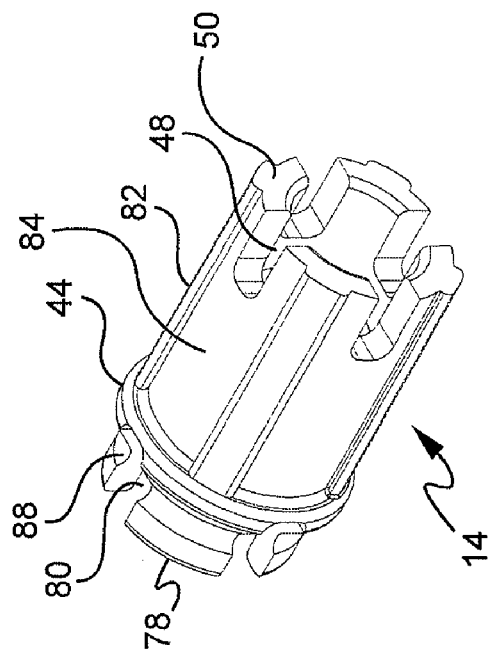
FIG. 21 is a perspective view showing the side and proximal end of the septum of FIG. 18.

Referring to FIG. 21, a proximal perspective view of the septum 14 shows the proximal end and side of the septum 14 with its various features.

Figure 22:
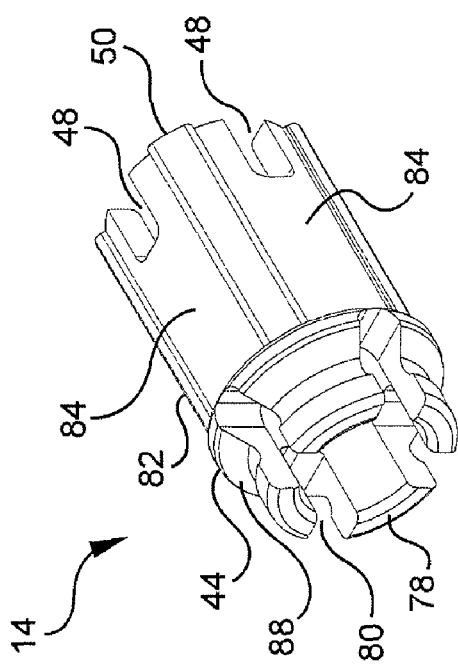
FIG. 22 is a perspective view showing the side and distal end of the septum of FIG. 18.

Referring to FIG. 22, a distal perspective view of the septum 14 shows the distal end and side of the septum 14 with its various features.

Figure 23:
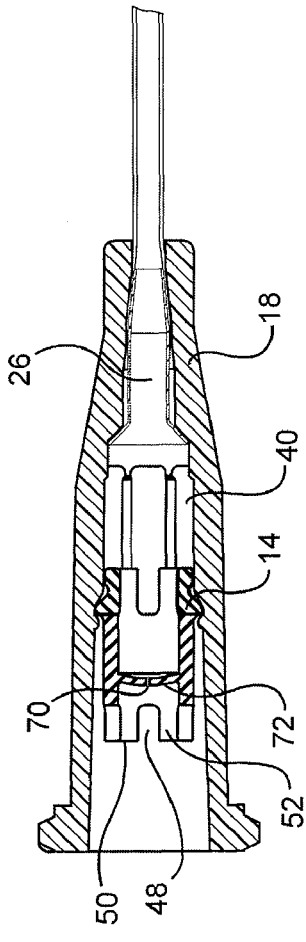
FIG. 23 is a cross section view of a portion of an extravascular system.
Figure 24:
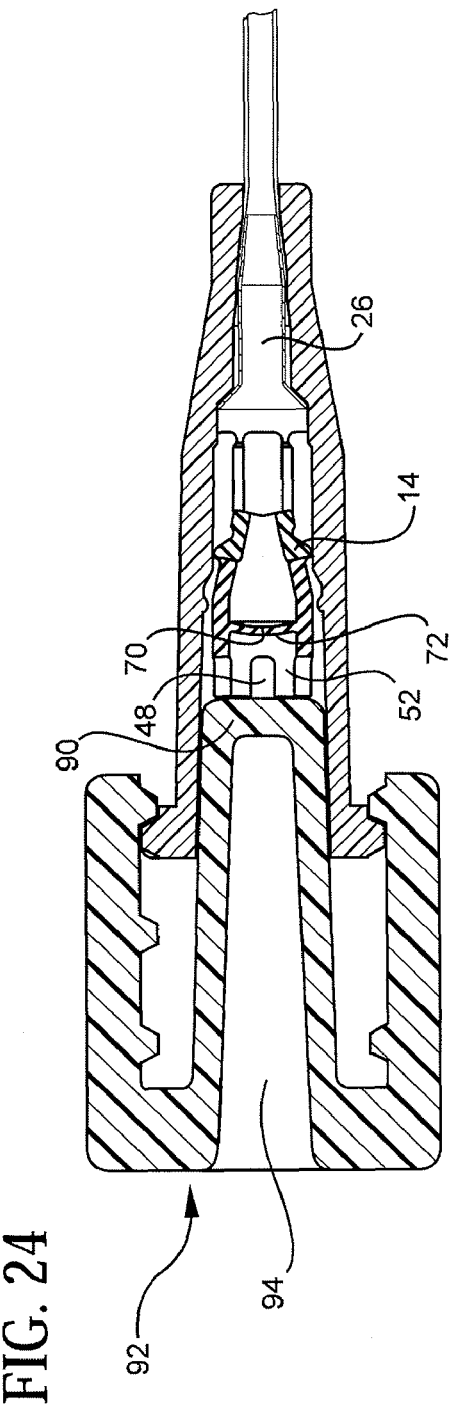
FIG. 24 is a cross section view of a portion of an extravascular system secured to a vascular access device.
Figure 25:
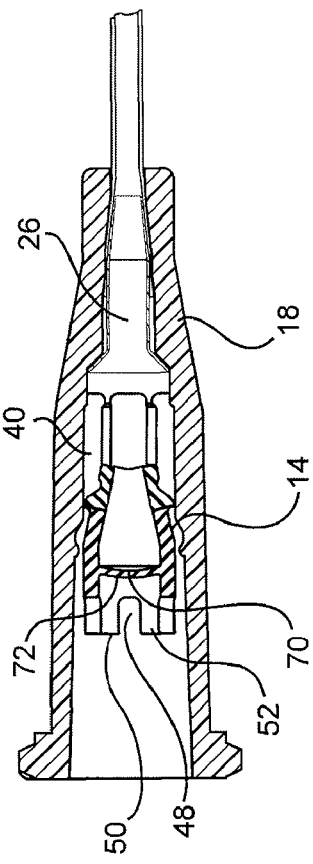
FIG. 25 is a cross section view of a portion of an extravascular system.

Referring collectively to FIGS. 23 through 25, a method of using an extravascular system 10 including a catheter housing 18 and septum 14 is described. In use, an operator or clinician will access the vasculature of a patient with the tip of a needle housed within the insertion portion of a catheter tubing 16. Upon insertion of the tip of the needle into the vasculature, blood will flow into the inner lumen of the cannula of the needle, out a small exit point within or near the distal end of the needle, between the catheter tubing 16 and the exterior surface of the cannula, and in a proximal direction along the extravascular system 10, giving the operator visual confirmation of proper placement of the needle tip within the vasculature of the patient. The blood will continue to flow along the inner lumen of the extravascular system 10 from the catheter tubing 16 into the wedge 26 and ultimately into the flash grooves 40. The flash grooves 40 may operate to meter the volumetric flow rate of the blood out of the proximal portion of the catheter housing 18 and permit continued tertiary flashback confirmation to an operator of the extravascular system 10.

As discussed briefly above, the extravascular systems of the present disclosure may be adapted to provide two or more configurations, including an insertion configuration. It is important for the clinician to observe the flashback of blood during the insertion process to ensure that the extravascular system is properly positioned in the vasculature. However, too much flashback can result in blood spilling or leaking out of the proximal end of the catheter assembly. Particularly problematic in conventional systems is the time period between withdrawal of the needle and attachment of another vascular access device, such as an IV line. Accordingly, as suggested above, the relationship between the retention construct 44 and the corresponding retention structure, such as flow grooves 40 and ridges 58, may provide a space through which fluid, including blood, may flow. More particularly, the relationship between the retention construct and the corresponding retention structure may provide a flow space adapted to meter the fluid flow to a desired rate.

Additionally, the retention construct and the corresponding retention structure may be adapted to provide a variable flow space dependent at least in part on the position of the internal construct within the catheter housing. For example, it may be desirable to provide one or more insertion configurations and one or more indwelling configurations. When the extravascular assembly 10 is being inserted into a patient's vasculature, it may be preferred to provide an insertion configuration adapted to meter the fluid flow rate through the flow space between the retention construct and the corresponding retention structures, such as to limit the flow of blood during flashback to avoid exposure. In some implementations, the retention construct and the corresponding retention structure may be adapted to allow a fluid flow rate within a predetermined, target insertion flow rate range. For example, while a particular target rate may be desired, variations between patients', such as varying blood pressures or other factors, may result in an extravascular system adapted to provide a flow space allowing a flow rate within a given range of the target rate. One exemplary target flow rate may correspond to a progression of the fluid at a rate of about one inch per minute. In some implementations, a suitable flow rate range may correspond to a progression of fluid at a rate of at least about one inch per minute. While faster and slower rates are acceptable, during insertion such faster or slower rates may complicate the procedures of the clinicians.

During the use of the extravascular system, volumetric flow rate of the fluids is important to control the volume of fluid passing through the system. Additionally, however, during insertion of the extravascular systems when the flashback is being controlled, it is important to control the progress of the fluid through the catheter assembly so as to reduce the likelihood of the fluid reaching the proximal end of the catheter assembly. As can be appreciated, the progress of the fluid through the catheter assembly in the flow space created by the relationship between the retention construct and the corresponding retention structure will be determined by the volumetric flow rate and the geometries of the flow spaces. As used herein, flow rate may refer to volumetric flow rates and/or flow rates measured by the progress of a fluid through a system.

At any point during blood flashback in the extravascular system 10, the catheter tip 22 of the catheter tubing 16 may be threaded into the vasculature of the patient and the needle may be removed from the extravascular system 10. As the needle is withdrawn, the slit 70 within the septal disk 72 removes blood from the needle on the distal side of the septal disk 72. When the needle is completely removed from the slit 70, the slit 70 seals the axial flow path. When the axial flow path through the axial center of the extravascular system 10 is completely sealed, blood is forced to travel around the exterior surface of the septum 14 through the flow grooves 40, providing continued flashback confirmation. It should be noted that during and after the withdrawal of the needle from the extravascular system, the internal construct 14 may remain in its insertion configuration to meter the flow of fluids past the internal construct. Accordingly, in implementations where the metered flow rate limits the progression rate of the fluid through the catheter housing, such limits may remain after the needle is withdrawn.

In most utilizations of an extravascular system 10, the catheter housing 18 will then be coupled to a vascular access device after the needle is withdrawn. As illustrated in FIG. 24, the catheter housing 18 is accessed with the male tip 90 of a separate vascular access device 92. As the tip 90 exerts force upon the contact surfaces 50 of the septum 14, the septum 14 is collapsed within the flow grooves 40 and forced in a distal direction to a second or indwelling configuration. In some implementations, multiple indwelling configurations may be available by forcing the septum 14 in the distal direction to a greater or lesser degree. As illustrated, moving the septum 14 in a distal direction will open the volume of the flow grooves 40 to a greater volume and provide the separate vascular access device 92 with less restricted vascular access through which the device 92 may infuse fluids. The fluids travel from the lumen 94 of the device 92 into a chamber 52 of the septum 14, from the chamber 52 through flow spaces 48, from the flow spaces 48 around the exterior surface of the septum 14 and through the flow grooves 40 distally towards the vasculature of a patient. After infusion, the device 92 may then be removed from the catheter housing 18 as shown in FIG. 25.

Thus, the embodiments described with reference to FIGS. 1 through 25 provide an extravascular system 10 having a compact, single component such as the septum 14 capable of collapsing upon Luer activation and operating as a valve that may be integrated into a number of catheter assemblies 12. Such catheter assemblies 12 may include any conventional vascular access device such as a peripheral, PICC, midline, and/or arterial catheter assembly. The septum 14 is located within the interior lumen 32 of the respective catheter assembly 12. A septum may act in part as a blood barrier sealing around the exterior surface of the cannula of a needle to prevent blood from passing through the central axis of the extravascular system 10. A septum engages the internal diameter of the catheter housing and also provides a range of motion within the lumen 32 of the catheter housing 18 capable of accommodating a variety of Luer penetration depths.

The septum 14 collapses into a flow groove 40 space of the barrel 34 when accessed by a Luer, providing a potential variation in fluid communication among the various fluid chambers of the extravascular system 10. The internal surface of the catheter housing and/or the external surface of the septum may include flow grooves to provide a primary path of blood and/or infusate fluid transfer before, during, and after the septum is activated or otherwise advanced distally within the lumen 32. The flash grooves on any surface within the extravascular system 10 may be formed as axial or other grooves that are capable of allowing blood to bypass the outer retention ring 44 of the septum 14, thus giving an operator of the extravascular system 10 a tertiary blood flashback confirmation at a controlled rate. The controlled rate may be carefully calculated and examples of such calculations will be described herein.

The embodiments described with reference to FIGS. 1 through 25 provide multiple advantages over conventional extravascular systems. For example, the extravascular system prevents uncontrolled amounts of blood from spilling out of the proximal end of the catheter housing 18 while not entirely eliminating blood flashback therein. Such blood flashback may continue to flow within visible chambers of the extravascular system 10 at a controlled rate, permitting an operator of the extravascular system 10 enough time to operate the extravascular system 10, exchange its preferred or necessary components or other vascular access devices. For example, as discussed above, a target flow rate may allow the blood to progress through the catheter housing at a rate of about one inch per minute. The controlled blood flow rate will prohibit blood from flowing through the extravascular system 10 at a rapid and uncontrolled rate capable of causing leaking or spilling during system 10 operation.

In addition, the internal septum 14 of the system 10 does not require a change in current clinical therapy of present extravascular systems. Rather, an operator of the system 10 may use the system 10 as the operator would any other extravascular system. However, the advantages of the present system will be available to such a system.

Further, the septum 14 and any equivalent or variation thereof may be employed within existing catheter platforms. And, as mentioned previously, the length of the barrel 34 accommodates various Luer access device penetration depths to provide an extravascular system 10 of relatively universal application. Since not all separate vascular access devices and/or male tips of Luer access devices are available in every country and/or clinical setting, a universal female Luer tip adapter on the proximal end of the catheter assembly 12 provides a significant advantage for the present invention.

Further, the controlled flashback features of the embodiments described with reference to FIGS. 1 through 25 present advantages over previous valves that are completely sealed and impede any flow of blood through an extravascular system. By providing controlled flow in the relatively unsealed system 10, an operator of the system 10 is provided with critical information necessary to properly locate, place, and maintain a needle and/or catheter tip within the vasculature of a patient during all steps of the operation of the extravascular system 10. Such continuous information is not available during all operative steps in other previous valves and/or extravascular systems. The septum 14 is a single component that also eliminates the need in previous systems to provide multiple components capable of piercing through the septum 14 and/or the slit 70 of the septum 14 in order to provide fluid access to a separate vascular access device after the septum 14 is activated. Because a septum 14 includes multiple fluid passageways such as the fluid spaces 48, fluid may flow into and around the septum 14 without any further obstruction after the septum 14 has been activated upon and towards flow grooves 40 having adequate volume to receive the infused fluid from the separate vascular access device. Thus, where previous systems would have sent the fluid flow through the central axis of the system 10, the present system 10 provides a primary flow path that is around the exterior surface of the septum 14.

In addition to the flow spaces 48 and/or holes formed within the walls of the body 82 of the septum 14, or as an alternate flow path thereto, other flash features such as holes through the internal septal disk 72 or other features that provide fluid communication between various fluid chambers of the system 10 at various steps of operation of the system 10 may be employed in order to provide fluid communication for blood flashback, blood withdrawal, and for fluid infusion into the vasculature of a patient.

The embodiments described with reference to FIGS. 1 through 25 and any other embodiments within the scope of the present invention enable the passage of air, blood, and/or other fluid to pass at a controlled rate with varying blood densities, viscosities, venous pressures, and/or atmospheric pressures. As described above, the flow rate around the internal construct 14 may vary depending on the intended usage of the extravascular system and the current operational configuration of the extravascular system. For example, when the extravascular assembly has been inserted and fluids are being infused or blood is being withdrawn, the flow rate around the valve of the septum 14 preferably may be greater than the flow rate within the catheter tubing 16 between the internal surface of the catheter tubing 16 and the external surface of the needle cannula, especially with regards to the flow of blood through the system 10. In the context of withdrawing blood for donation or analysis, the sheer and exposure time may be minimized in order to prevent hemolysis by ensuring that the catheter tubing 16 is the flow rate limiter within the system 10. Thus, the geometry of the various flow spaces within the extravascular system may be defined to allow for the catheter tubing 16 to be the flow rate limiter rather than other portions of the system 10. However, various other portions of the system 10 may become the flow rate limiter in order to achieve various alternate objectives of a system 10, such as to control the flashback rate. Various calculations may be performed in order to determine appropriate size of various flow channels within the extravascular system 10 in order to achieve the principles discussed herein. Exemplary equations and calculations are presented below together with exemplary values for the variables of the equations. While the calculations presented below are illustrative of the methods of using the equations, they may not be representative of the variable values or results of extravascular assemblies. For example, the flow rates, sizes, and other values may vary from those presented herein.

The following equations may be used to size the flow and/or flash grooves 40 and/or any other channel through which fluid may flow in an extravascular system 10 in order to minimize hemolysis, maximize flow rate through the system 10, and/or allow controlled flashback of blood prior to access by a separate vascular access device 92. The following calculations assume fluid properties that are similar to blood, including viscosity and density, such as $H_2O$ with glycerin. The following calculations also assume that the atmospheric pressure at the tip of the catheter tubing 16 is at zero pounds per square inch (psi) both before and just prior to insertion into the vascular system of a patient.

The flow rate through the extravascular system 10 may be limited by the configuration of any one or more flow spaces. As discussed above, in some implementations or during certain phases of use, it may be preferred for the flow rate to be limited at least in part by the internal construct 14 and in other circumstances it may be preferred for the flow rate to be limited primarily by the catheter tubing 16. One critical flow space includes the flow rate through the flow grooves 40 adjacent or near the septum 14. The flow rate through the area of the flow grooves 40 may be calculated using the following equation:

$$Q = \frac{\pi \cdot deq^4 \cdot (P3 - P2)}{128 \cdot \mu \cdot L \cdot K3\_2}$$

where Q equals the flow rate through the flow grooves 40.

In the above equation, deq is the equivalent diameter of the area of all flow grooves 40 combined. The equivalent diameter of the area of the flow grooves 40 may be calculated using the following calculation:

$$deq = \sqrt{\frac{4 \cdot A}{\pi}}$$

where A equals the flow groove area, which is calculated by measuring the dimensions of the flow grooves 40 when the septum 14 is in a given position. It should be noted that the flow groove area A may vary when the septum is in different positions, such as an insertion configuration compared to an indwelling configuration, and the flow rate through the grooves Q will vary accordingly. The variable P3 is an arbitrary pressure which may exist within the extravascular system 10. The variable P2 is the atmospheric pressure. The variable µ equals $$0.0002 \frac{lb}{in \cdot s}$$

and represents parameters of simulated blood flow through the flow grooves 40. The variable L represents the length along the flow grooves 40 through which fluid must flow in order to pass the entire length of the septum 14. The variable K3_2 represents the loss factor moving from the proximal end of the wedge 26 to the proximal end of the septum 14. The loss factor may be calculated along any length within the extravascular system 10. In common extravascular systems 10, the loss factor includes multiple 90 degree bends and fluid transitions from a reservoir into a channel and from a channel into a reservoir. Other factors may be included within the loss factor calculation.

In an illustrative example, the variable A may equal 0.0054 inches squared and the pressure values may provide P3 equal to 0.922 psi and P2 equal to 0 psi. As indicated, the variable µ represents a parameter determined from simulated blood flow through the grooves, and may be equal to $$0.0002 \frac{lb}{in \cdot s}.$$

The length L may be any suitable measurement, and for purposes of this illustration may be equal to 0.2043 inches. Continuing with the illustrative calculation, the loss factor calculation is 7.5 for each of six separate flow grooves 40, yielding a total loss factor (K3_2) of 45. Applying the values of the variables in the equation above to calculate flow rate (Q) yields a result of Q equals $$241.2245 \frac{mL}{min}.$$

the flow rate of 241.2245 is the volumetric flow rate of fluid, which may be blood or another comparable fluid such as intravenous fluids, as it exits the flow grooves 40 between the exterior surface of the septum 14 and the interior surface of the catheter housing 18 and at the proximal end of the septum 14.

In addition to determining the flow rate (Q) through the flow grooves 40 in the presence of a septum 14, one may desire to determine the flow rate through the catheter tubing 16 within the system 10 in the absence of a septum 14. Such a calculation will reveal the maximum flow rate through the system 10 in the absence of a septum 14 and may be used to reduce the risk of contaminating or spoiling fluids passing through the catheter, such as blood withdrawn for analysis or donation and/or infused fluids. Where the flow rate in the absence of a septum 14 is the same as or similar to the flow rate through a common catheter assembly, equations for determining this flow rate have been researched and published previously, such as by M. Keith Sharp, "*Scaling of Hemolysis in Needles and Catheters*", Annuals of Biomedical Engineering, Vol. 26, pp. 787-797, 1998. One suitable method of calculating this flow rate, identified as variable $Q_c$ may use the following equation:

$$Q_c = \frac{\pi (d1)^4 \cdot (P3 - P1)}{128 \cdot \mu \cdot L1\_2 \cdot K1\_2}.$$

The variable d1 is the inner diameter at the most distal tip of the catheter tubing 16, which for purposes of calculation may be assumed to creep or approach the outer diameter of a cannula of a needle that would function with the catheter tubing 16. The inner diameter of the catheter tubing 16 at the most distal tip of the catheter tubing 16 will vary depending on the gauge of needle that is used in combination with the particular tubing 16. Multiple needle gauges from 14 through 24 and their associated catheter tubing 16 diameters are illustrated in the following table.

TABLE 1

| d1 | Product Gauge |
|---|---|
| 0.0648 | 14.0000 |
| 0.0488 | 16.0000 |
| 0.0348 ·in | 18.0000 |
| 0.0283 | 20.0000 |
| 0.0223 | 22.0000 |
| 0.0163 | 24.0000 |

The variables P3 and P1 include different pressures both within the system 10 (P3) and at the most distal tip of the catheter 16 (P1). These pressures may include various values, such as 0.922 psi for variable P3 and 0 psi for variable P1. The variable µ may include the same value as described earlier, that is, $$0.0002 \frac{lb}{in \cdot s}.$$

The variable L1_2 represents the length of the catheter tubing 16 from its most distal tip to its most proximal end. For example, the length from tip 22 to the proximal end of the proximal taper 30 as shown in FIG. 1, may vary from one system 10 to another depending upon the specific gauge of the needle employed with the catheter tubing 16. The following table sets forth examples of various values of the length of the catheter tubing with corresponding needle gauges.

TABLE 2

| L1_2 | Product Gauge |
|---|---|
| 2.204 | 14.0000 |
| 2.204 | 16.0000 |
| 2.204 ·in | 18.0000 |
| 2.204 | 20.0000 |
| 1.379 | 22.0000 |
| 1.079 | 24.0000 |

The variable K1_2 represents the loss factor across the length of the catheter tubing 16. The loss factor K1_2 may be calculated using the following calculation.

$$K1\_2 = f \cdot \frac{L1\_2}{d1}$$

The variable f within the calculation above represents the friction factor across the length of the catheter tubing 16. The friction factor, similar to variables d1 and L1_2, will vary depending on the needle gauge employed with the catheter tubing 16. The following table illustrates various friction factors that correlate to various needle gauges taken from M. Keith Sharp, "*Scaling of Hemolysis in Needles and Catheters*", Annuals of Biomedical Engineering, Vol. 26, pp. 787-797, 1998. The friction factor corresponding to each needle gauge is representative of the friction factor across the length of a corresponding catheter tubing.

TABLE 3

| f | Product Gauge |
|---|---|
| 0.028 | 14.0000 |
| 0.049 | 16.0000 |
| 0.064 ·in | 18.0000 |
| 0.070 | 20.0000 |
| 0.075 | 22.0000 |
| 0.080 | 24.0000 |

Using the equation above to calculate the loss factor across the length of the catheter tubing 16, various values that correspond to various needle gauges may be calculated for the variable K1_2, as shown in the following table.

TABLE 4

| K1_2 | Product Gauge |
|---|---|
| 0.9523 | 14.0000 |
| 2.2130 | 16.0000 |
| 4.0533 ·in | 18.0000 |
| 5.4516 | 20.0000 |
| 4.6379 | 22.0000 |
| 5.2957 | 24.0000 |

By incorporating each of the values for the variables above into the equation to calculate volumetric flow rate leaving the catheter 22 without a septum 14, that is, the flow rate $Q_c$, will yield the results illustrated in the table below.

TABLE 5

| $Q_c$ | | Product Gauge |
|---|---|---|
| 394.0835 | | 14.0000 |
| 54.5474 | | 16.0000 |
| 7.7017 | ·in | 18.0000 |
| 2.5044 | | 20.0000 |
| 1.8140 | | 22.0000 |
| 0.5796 | | 24.0000 |

By comparing the results for the flow rate Q and the flow rate $Q_c$ in the examples above, it is apparent that the flow rate Q through the flow grooves 40 of $$241.2245 \frac{mL}{min}$$

is greater than the flow rate $Q_c$ through the catheter tubing 16 for all gauge sizes with exception of a 14 gauge needle. Accordingly, the parameters and values used in the illustrative example for determining flow rate Q may correspond to an extravascular system configured in an indwelling position in which the fluid flow is relatively unrestricted or unmetered by the internal construct 14. In some implementations, it may be preferred to ensure that the catheter tubing 16 and/or catheter tip 22 is the flow rate limiter rather than the septum 14 when in an indwelling position. Accordingly, the illustrative example above may be suitable for use with 16 gauge needles and smaller. For 14 gauge needles and larger, the area of the flow grooves 40 or any other flow channels may be increased sufficient to ensure that the catheter tip 22 and/or catheter tubing 16 is the flow rate limiter within the system 10, when such a configuration is desired, such as to minimize hemolysis and/or to maximize flow rate. However, as mentioned above, in other implementations or during other phases of use, it may be preferred to control and meter the fluid flow rate through the catheter housing by way of the internal construct 14 applying flow restrictions.

Figure 26:
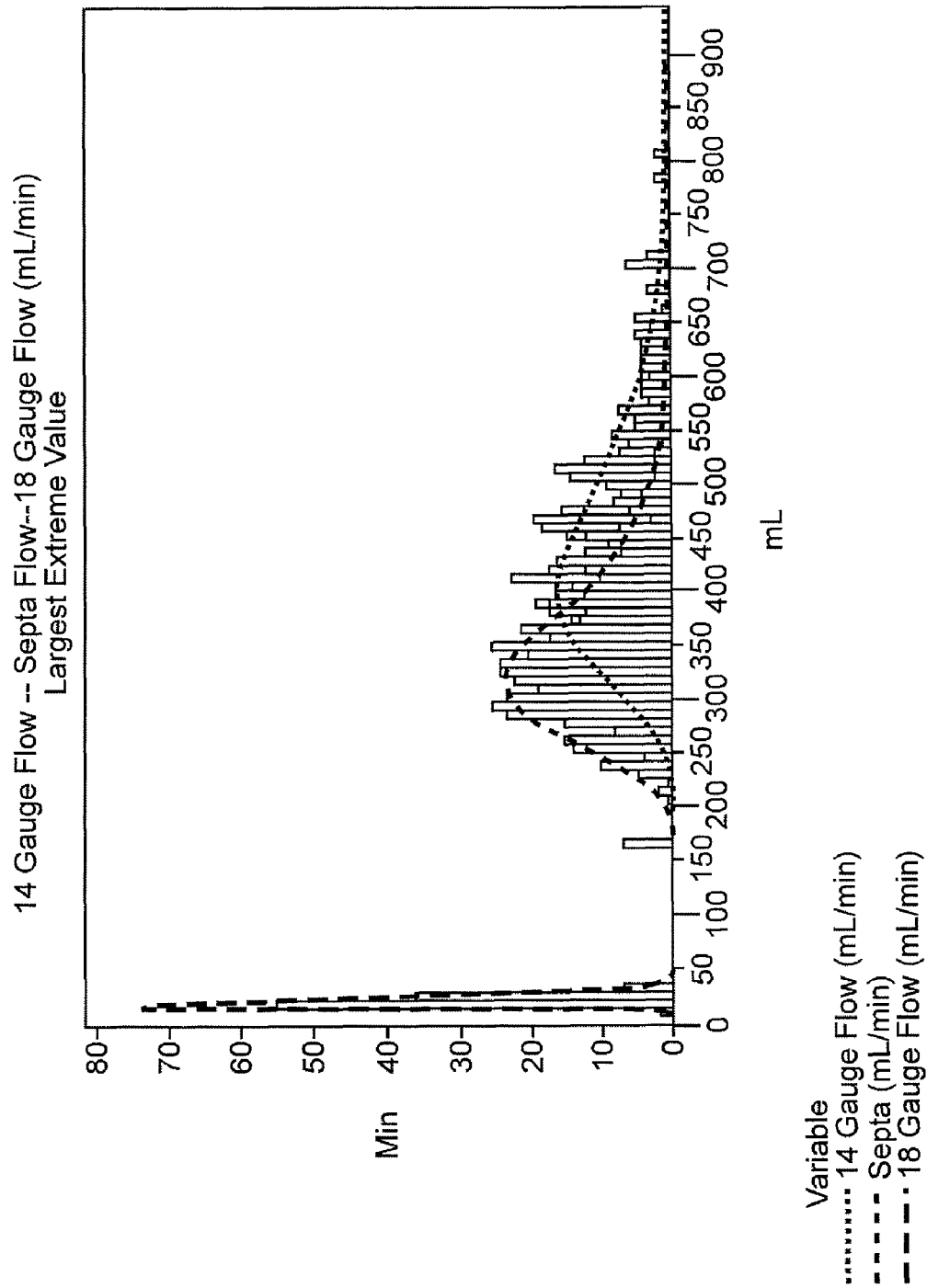
FIG. 26 is a graph comparing various fluid flow rates within an extravascular system.

Referring to FIG. 26, results similar to those calculated above are illustrated in a chart comparing flow within a catheter tubing 16 accommodating a 14 gauge needle, flow within a catheter tubing 16 accommodating an 18 gauge needle, and the flow within the grooves 40 surrounding a septum 14. The results indicated in the chart of FIG. 26 again confirm that the flow rate through the flow grooves 40 surrounding the septum 14 is greater than the flow rate through a catheter tube 16 accommodating an 18 gauge needle but not greater than the flow rate through a catheter tubing 16 accommodating a 14 gauge needle. In addition to calculating and comparing various flow rates within the extravascular system 10, calculations determining the blood shear stress and exposure time across the flow grooves 40 near the septum 14 may be helpful in order to determine the expected level of hemolysis within the system 10. Determining the expected level of hemolysis within the flow grooves 40 may enable a manufacturer of the system 10 to determine the appropriate flow groove dimensions and area. The hemolysis of the flow grooves 40 may be calculated by a constant C·exp(S), where the variable S represents the exposure to sheer stress that may be calculated using the following equation.

$$S = \frac{t\_fg}{t_o}\left(\frac{\tau\_fg}{\tau o} - 1\right)^2$$

The variable t_fg may be calculated using the following calculation, which measures the blood exposure time to sheer stress.

$$t\_fg = \frac{32 \cdot \mu \cdot L^2}{(P6 - P5) \cdot deq^2}$$

The variables μ, L, and deq have already been defined previously. The variable P5 equals 0 psi and the variable P6 equals 69000 Pa (the vapor pressure of blood, or the maximum vacuum which may be pulled on a syringe before causing cell damage within blood). Applying the values previously mentioned herein to the variables of the equation above yields a result of t_fg equals $1.64 \times 10^{-5}$ seconds for the blood exposure time to sheer stress. It should be noted that the value of t_fg will vary depending on the input variables, such as the flow area (deq) and the length (L); in general it has been observed that t_fg may have any value greater than $1 \times 10^{-6}$. The variable $t_o$ equals 0.0158 seconds. The variable τ_fg may be calculated to determine the sheer stress of blood in the flow channels 40 using the following equation.

$$\tau\_fg = \frac{(P6 - P5) \cdot deq}{4 \cdot L}$$

The result of the above equation is τ_fg equals $$70012.0303 \frac{dyne}{cm^2}.$$

The variable τo is $$1500 \frac{dyne}{cm^2}.$$

Applying the values above to the variables of the equations above yields a result for the hemolysis within the flow grooves 40 equal to $$5.7664 \frac{mg}{dl}.$$

Because the hemolysis level of $$5.7664 \frac{mg}{dl}$$

is below $$10 \frac{mg}{dl}$$

(the threshold of visual hemolysis) and below $$30 \frac{mg}{dl}$$

(the threshold in which no interference occurs with chemical assays), the area of the flow grooves 40 in the example above is sufficient to maintain a desired level of hemolysis.

The illustrative calculations above are generally directed towards determining the flow rates and conditions when the septum 14 is positioned in an indwelling configuration, which generally provides greater flow rates and larger flow spaces. However, such calculations and similar calculations may also be helpful in determining the operating conditions and/or manufacturing specifications for configuring the extravascular system 10 in an insertion configuration adapted to meter fluid flow with the internal construct 14. For example, it may be desirable to determine the amount of time an operator may permit blood to flow through the system 10 before blood begins to spill out of the proximal end of the system 10. The calculation of the amount of time needed for blood to travel from the distal most tip of the catheter tubing 16 to the most proximal end of the catheter housing 18 may be included in calculation and consideration of multiple variables, such as the venous pressure, the atmospheric pressure, the length of the septum 14, the area of the flash grooves 40, the loss factor moving across the length of the system 10, the volumetric flow rate of blood through the system 10, and the total volume within the system 10 capable of housing blood. Similar to the discussion above, illustrative calculations utilizing exemplary values for the variables are provided below. While the exemplary values for the variables used below may be accurate for some implementations, other extravascular systems 10 within the scope of the present disclosure may provide different results. For example, the examples below produce a total time of 0.3982 seconds to fill the space in the inner chamber 32 between the proximal end of the septum 14 and the proximal end of the catheter housing 18. However, other systems may take more time to fill the same. Exemplary extravascular systems 10 within the scope of the present disclosure may provide an insertion configuration adapted to provide a flow rate corresponding to a fluid progression rate of about one inch per minute, as discussed above.

The time to fill the space within the chamber 32 will be calculated by the total fill volume (fill_volume) divided by the flow rate (Q_vg) of fluid within the system 10. The following examples of equations and variables may be employed within a calculation to determine the time to fill the space within the end of the chamber 32.

$$P\_v = 0.5 \cdot psi \text{ (Average Venous Pressure)}$$

$$P\_rs = 0 \cdot psi \text{ (Venting to Atmosphere)}$$

$$L = 0.2043 \cdot in \text{ (Valve Length)}$$

$$A\_vg = 0.001 \cdot in^2 \text{ (Flash Groove Area)}$$

$$deq\_vg = \sqrt{\frac{4 \cdot A\_vg}{\pi}} \quad deq\_vg = 0.0357 \text{ in}$$

$$Q\_vg = \frac{\pi \cdot deq\_vg^4 \cdot (P\_v - P\_rs)}{128 \cdot \mu \cdot L \cdot K\_fg}$$

$$Q\_vg = 7.4769 \frac{mL}{min}$$

$$L\_hub = 0.135 \cdot in$$

$$D\_hub = 0.169 \cdot in$$

$$Fill\_Volume = \frac{\pi}{4} \cdot d\_hub^2 \cdot L\_hub$$

$$Fill\_Volume = 0.0496 \text{ mL}$$

$$Time\_To\_Fill\_the\_Hub = \frac{Fill\_Volume}{Q\_vg}$$

$$Time\_To\_Fill\_the\_Hub = 0.3982 \text{ s}$$

The loss factors mentioned in any of the calculations above may include any environment within the system 10 capable of causing a variation in friction. For purposes of simplicity, the 90 degree bends, reservoir to channel entrance, and channel to reservoir entrance have been used. However, any variety of frictional loss factors capable of calculation may be used such as frictional loss factors at valves, 180 degree return bends, pipe entrances (reservoir to pipes), elbows, tees, pipe exits (pipe to reservoir), and/or any other frictional loss factor environment. Such frictional loss factor environments may include globes, angles, gates, spring checks, flanged and/or threaded return bends, square connections, rounded connections, re-entries, 90 degree angles, 45 degree angles, line flows, branch flows, and/or any other frictional loss factor environmental structure.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A catheter assembly comprising:
    a catheter housing;
    a septum housed within the catheter housing, the septum being movable between a first position and a second position within the catheter housing, the septum dividing a distal chamber of the catheter housing from a proximal chamber; and
    at least one flow groove between an internal surface of the catheter housing and an external surface of the septum.

2. The catheter assembly of claim 1, wherein the at least one flow groove varies in depth along the length of the flow groove.

3. The catheter assembly of claim 2, wherein the at least one flow groove extends along the entire length of the septum.

4. The catheter assembly of claim 3, wherein the at least one flow groove includes at least six flow grooves.

5. The catheter assembly of claim 2, further comprising a retention construct and a corresponding retention structure in communication with the catheter assembly and the septum, wherein the retention construct and the corresponding retention structure are capable of at least temporarily retaining the septum in the first position.

6. The catheter assembly of claim 5, wherein the corresponding retention structure includes a retention space that permits fluid to flow past the retention construct when the retention construct is engaged with the corresponding retention structure.

7. The catheter assembly of claim 1, wherein the septum has a septal disk.

8. The catheter assembly of claim 5, wherein the retention construct is an annular retention ring protruding from an exterior surface of the septum, and the corresponding retention structure is an annular retention space.

9. The catheter assembly of claim 8, wherein in the first position fluid flows between the annular retention ring and the at least one flow groove at a rate of about one inch per minute.

10. The catheter assembly of claim 8, wherein in the second position fluid flow between the annular retention ring and the at least one flow groove at a faster rate than when the septum is in the first position.

11. The catheter assembly of claim 1, wherein the septum is of unitary construction.

12. The catheter assembly of claim 1, wherein various separate vascular access devices may be employed with the catheter assembly and wherein the septum is positioned within the catheter housing to accommodate for various lengths of the separate vascular access devices that may be employed with the catheter assembly.

13. An extravascular system for accessing the vasculature of a patient, comprising:
   a catheter assembly including a catheter housing and a catheter tubing secured to the catheter housing;
   a septum housed within the catheter housing, the septum including an external surface;
   an annular ring protruding from an exterior surface of the septum, the annular ring being movable between a first position and a second position within the catheter housing as the septum moves within the catheter housing;
   at least one flow groove formed into an internal surface of the catheter housing, wherein the at least one flow groove extends between the first and second positions of the annular ring and varies in depth along the length of the flow groove.

14. The extravascular system of claim 13, further comprising an annular space formed on the internal surface of the catheter housing capable of at least temporarily retaining the septum in the first position.

15. An extravascular system for accessing the vasculature of a patient, comprising:
   a catheter housing having an interior lumen and a longitudinal axis, the interior lumen having a interior surface;
   a septum housed within the interior lumen of the catheter housing, the septum dividing a distal chamber of the catheter housing from a proximal chamber, the septum having an exterior surface with a retention ring protruding therefrom, the retention ring being movable between a first and a second position within the catheter housing; and
   a flow groove between the interior surface of the interior lumen and the exterior surface of the retention ring, the area between the flow groove and the retention ring defining a flow area, wherein the flow groove varies in depth along the length of the flow groove, wherein the flow area varies as the retention ring moves along the longitudinal axis of the catheter housing between the first and second positions.

16. The extravascular system of claim 15, further comprising an annular space formed on the internal surface of the catheter housing capable of at least temporarily retaining the septum in the first position.

17. The extravascular system of claim 16, wherein the flow groove is deeper than the annular space to permit fluid flow past the annular ring when the annular ring is engaged within the annular space.

18. The extravascular system of claim 15, further comprising at least one additional flow groove between the interior surface of the interior lumen, the exterior surface of the retention ring and the flow grooves defining the flow area, wherein the at least one additional flow groove varies in depth along the length of the flow groove.

19. The extravascular system of claim 15, wherein the flow groove is formed into the internal surface of the catheter housing.

20. The catheter assembly of claim 1, wherein the at least one flow groove is formed into the internal surface of the catheter housing.

21. The catheter assembly of claim 13, wherein the at least one flow groove includes at least two flow grooves.

22. The catheter assembly of claim 14, wherein the at least one flow groove is deeper than the annular space to permit fluid flow past the annular ring when the annular ring is engaged within the annular space.

* * * * *